United States Patent [19]

Koledin

[11] Patent Number: 5,121,756
[45] Date of Patent: Jun. 16, 1992

[54] VACUUM IMMOBILIZER SUPPORT
[75] Inventor: Michael J. Koledin, Escondido, Calif.
[73] Assignee: Hartwell Medical Corporation, San Marcos, Calif.
[21] Appl. No.: 556,733
[22] Filed: Jul. 20, 1990

Related U.S. Application Data

[63] Continuation-in-part of Ser. No. 425,955, Oct. 10, 1989, abandoned.

[51] Int. Cl.⁵ .................. A61F 5/37; A61G 1/00
[52] U.S. Cl. ..................... 128/870; 128/DIG. 20; 602/6
[58] Field of Search .......... 128/78, 845, 870, DIG. 20, 128/84 C, 85, 87 R, 87 B, 89 R, 89 A, 869

[56] References Cited

U.S. PATENT DOCUMENTS

| | | | |
|---|---|---|---|
| 2,489,828 | 11/1949 | Springer | 5/82 R |
| 2,655,916 | 10/1953 | Timmins | 128/87 R |
| 2,766,751 | 10/1956 | Topa | 128/870 |
| 3,135,972 | 6/1964 | Jakes et al. | 5/82 R |
| 3,158,875 | 12/1964 | Fletcher | 5/82 R |
| 3,212,497 | 10/1965 | Dickinson | 128/87 R |
| 3,232,289 | 2/1966 | Zimmerman | 128/87 R |
| 3,399,670 | 9/1968 | Veasey | 128/870 |
| 3,740,777 | 6/1973 | Dee | 128/845 X |
| 3,745,998 | 7/1973 | Rose | 128/89 R |
| 3,762,404 | 10/1973 | Sakita | 128/78 |
| 3,814,088 | 6/1974 | Raymond | 128/87 R |
| 4,024,861 | 5/1977 | Vincent | 128/87 R |
| 4,045,830 | 9/1977 | Loeb et al. | 5/81 R |
| 4,127,120 | 11/1978 | Applegate | 128/870 |
| 4,141,368 | 2/1979 | Meyer | 128/870 X |
| 4,182,320 | 1/1980 | Sweeney | 128/89 R |
| 4,211,218 | 7/1980 | Kendrick | 128/870 X |
| 4,234,982 | 11/1980 | Bez et al. | 5/455 |
| 4,261,349 | 4/1981 | Lamsson et al. | 128/89 R |
| 4,301,791 | 11/1981 | Franco, III | 128/DIG. 20 |
| 4,428,087 | 1/1984 | Horn | 5/449 |
| 4,492,225 | 1/1985 | Picolet et al. | 128/87 R |
| 4,580,555 | 4/1986 | Coppess | 128/89 R |
| 4,657,003 | 4/1987 | Wirtz | 128/869 |
| 4,665,908 | 5/1987 | Calkin | 128/88 X |
| 4,766,890 | 8/1988 | Hollrah | 128/89 R |

FOREIGN PATENT DOCUMENTS

| | | | |
|---|---|---|---|
| 275320 | 7/1988 | European Pat. Off. | 128/87 R |
| 2602492 | 7/1976 | Fed. Rep. of Germany | 128/87 R |
| 1591024 | 6/1981 | Fed. Rep. of Germany | 128/845 |
| 160799 | 9/1964 | U.S.S.R. | 128/87 R |

OTHER PUBLICATIONS

Evac-U-Splint Publication.
Vacuum Splint Publication (Japanese).
Vacuum Fixer Publication (Japanese).
Zimfoam, Journal of Bone & Joint Surgery, vol. 50-B, No. 2, May 1968, advertisement.

Primary Examiner—Robert A. Hafer
Assistant Examiner—Kevin G. Rooney
Attorney, Agent, or Firm—Joseph F. McLellan

[57] ABSTRACT

A vacuum immobilizer support is disclosed which includes an elongated, flexible casing having neck, thoracic and pelvic regions. An evacuation valve is provided to allow the casing to be converted from a flexible state to an evacuated state. Stiffener sections are provided in the casing to prevent transverse bending of the casing in the neck, thoracic and pelvic regions. The stiffener sections allow transverse bending along an axis between the thoracic and pelvic regions. An intermediate stiffener section is provided to prevent longitudinal shortening of the casing between upper and lower stiffener sections. Discrete elements are disposed within the casing and allow the casing to conform to a patient when in its flexible state and to be rigidly fixed when in its evacuated state.

7 Claims, 4 Drawing Sheets

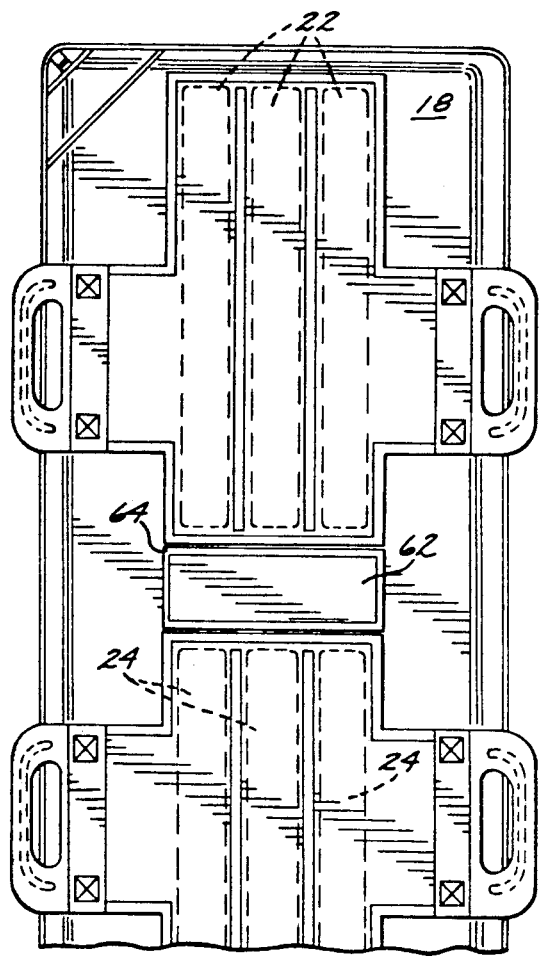
FIG. 10
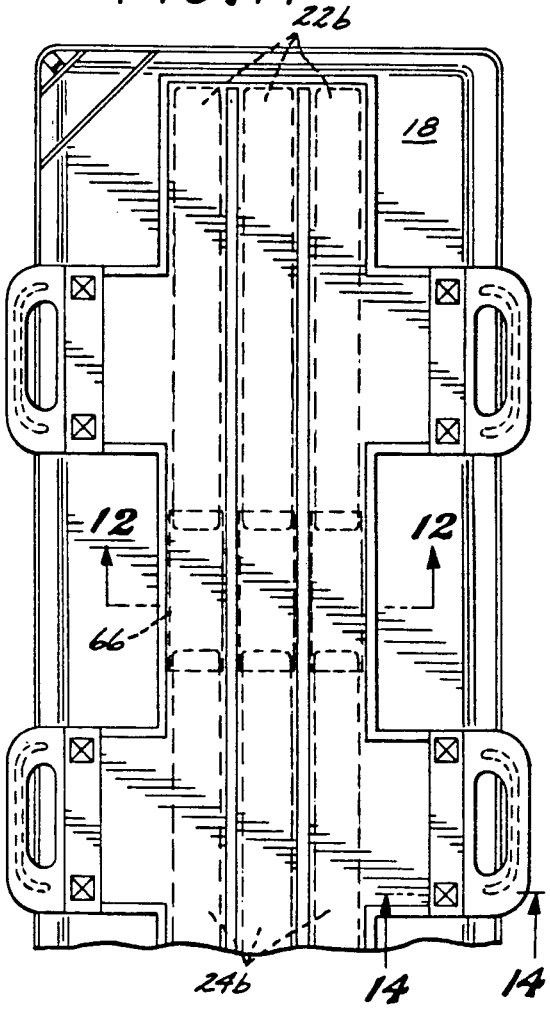
FIG. 11
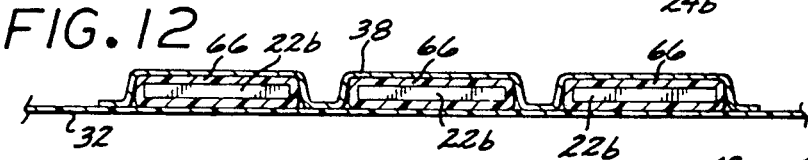
FIG. 12
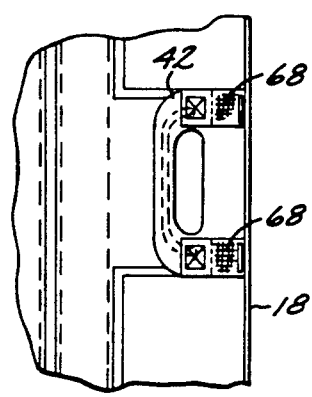
FIG. 13
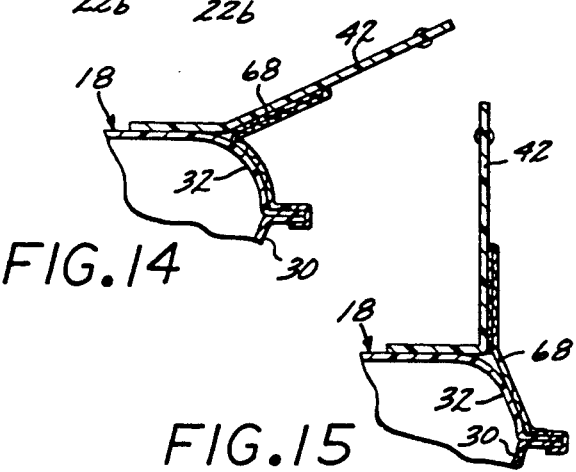
FIG. 14
FIG. 15

VACUUM IMMOBILIZER SUPPORT

CROSS REFERENCE TO RELATED APPLICATION

This application is a continuation-in-part of my copending patent application Ser. No. 07/425,955, filed Oct. 10, 1989 abandoned.

BACKGROUND OF THE INVENTION

1. Field of the Invention

The present invention relates to a vacuum immobilizer support for maintaining a person in an immobilized state.

2. Description of the Prior Art

Transportation of accident victims in an immobilized state is widely recognized as important to prevent secondary trauma, and particularly injury to the spinal cord. Not so well recognized are the important benefits which can be achieved in immobilizing other classes of patients.

In-hospital transportation of patients from their rooms to other areas of the hospital for special diagnostic procedures or for special treatment involves a number of changes in patient position, any one of which could aggravate existing medical afflictions. The patient must be lifted and transferred from bed to gurney or wheelchair, transported to the desired area, and in like manner must be physically moved about for diagnosis or treatment, etc. and then returned to his or her room. Where immobilization is critically important, as in spinal injury cases, the patient is typically strapped down firmly onto a wooden backboard which is then placed on the gurney. Even this does not always prevent secondary trauma from occurring because of lateral forces acting on the patient during turning of the gurney or tipping of the backboard, for example.

Trauma also develops because the weight of the patient is unevenly distributed over the hard backboard. The prominent bones of the body rest upon the board, developing pressure points, while the body structure between these pressure points is relatively unsupported. Bedridden patients also suffer from the effects of these pressure points over a long period of time.

What has just been said about the desirability of better immobilization of patients lying or transported in a prostrate position also applies to patients in wheelchairs. In fact, it is sometimes even more difficult to avoid aggravation of preexisting injuries when moving patients into and out of wheelchairs, or into and out of vehicles. There is presently no completely effective way to immobilize accident victims or patients in emergency or hospital situations, or to immobilize the aged, the infirm or the orthopedically impaired who are wheelchair bound or bedridden.

There has been a trend toward the provision of padding on backboards at usual pressure points, or the covering of such boards with a padding sleeve. This has been effective in reducing bruising and other secondary trauma, but only at the sacrifice of optimum immobilization.

Recent studies have suggested the importance of proper patient immobilization following an accident. Fully twenty percent of paraplegia has been attributed to improper handling of victims following the accidents.

The victims of Marfan Syndrome are a tragic example of the need for adequate patient immobilization. This genetic disease affects the connective tissue of the skeleton, lungs, eyes, heart and other organ systems such that the tissue does not hold the body parts in proper position. When the joints cannot be held in position the body will not support its own weight and the patient becomes bedridden. Attempts to transport such patients have resulted in dislocated joints, followed by days of pain and severe swelling until the joints have returned to their normal positions. This has occurred even when the patient has been transported within a protective cast resting upon layers of cushioning material.

One of the better immobilization means of the prior art is a vacuum or air evacuated bag or casing which is filled with small discrete elements such as round beads. The bag completely underlies the patient and is made wide enough to come up along the sides of the patient for cradling and supporting the body. When air is evacuated from the bag the bag becomes rigid and immobilizes the patient in a protective cocoon.

The arrangement has serious shortcomings. Evacuation of the bag is accompanied by longitudinal shrinking or shortening of the bag which undesirable causes spinal compression.

Further, the bag tends to be structurally prone to transverse bending when it is the sole means used to transport a patient. This tendency is alleviated if the bag is made wide enough to substantially encircle the patient. This produces a cylindrical configuration that does not bend easily, but the extra width of such a bag presents storage problems for paramedics who have limited space available in emergency vehicles.

Thus, although this form of vacuum bag tends to satisfactorily immobilize a patient, it is not well suited to use by paramedics, and it has apparently not been suggested how it could be modified to suit the needs of that larger class of persons who are in need of proper immobilization in bed, in wheelchairs, and during in-hospital handling and transportation.

SUMMARY OF THE INVENTION

According to the present invention, an alternately collapsible and rigidifiable vacuum immobilizer is provided which combines the good features of both a rigid spineboard or backboard and the known forms of vacuum immobilizer.

The present vacuum immobilizer support comprises an elongated, airtight and flexible casing upon which a patient can be placed. The casing includes specific regions adapted to underlie the neck, thorax and pelvis of the body. Discrete elements or beads partially fill the interior of the casing, and air evacuation valve means are provided to develop a vacuum to convert the casing from a relatively flexible state to a rigid, evacuated state.

The casing can be but need not be wide enough to encircle or overlie the patient. Stiffener means associated with the casing provide resistance to transverse bending during handling and transportation of a patient, and also act to prevent longitudinal shortening of the casing when it is evacuated.

In one embodiment the stiffener means comprises transversely spaced apart slats or narrow boards or battens disposed in two sets of pockets which are longitudinally spaced apart and extend longitudinally through the neck and thoracic regions, and through the pelvic region, respectively. These battens prevent any transverse bending or pivotal movement of the casing in these regions in the rigidified state of the casing. However, their transverse spacing permits the casing to be wrapped or pivoted about longitudinal axes to conform the unevacuated casing to the contours of the patient.

The two sets of battens are preferably longitudinally spaced apart slightly to enable relative bending of the unevacuated casing between them. The casing can be fitted to a patient in a seated position. Evacuating the casing then permits the patient to be transported in a sitting position, or transferred to a wheelchair. Alternatively, the unevacuated casing can first be placed on a wheelchair, the patient then seated upon the casing, and the casing then evacuated to immobilize the seated patient.

In another embodiment an additional, transversely oriented stiffener is placed between the two sets of battens just described. This locates it in the region adjacent the base of the patient's spine, providing additional immobilization and support in that region. It also positively constrains the casing against longitudinal shrinkage in that region.

To further ensure against transverse bending of the casing in its rigidified state, the carrying handles for the casing are precisely located adjacent the critical regions. One pair of handles is mounted to the casing on opposite sides of the thoracic region, and another pair on opposite sides of the pelvic region. When the casing is lifted the weight of the patient is then distributed to the sets of battens located in those regions and no bending occurs between them.

Use of the stiffening means and carrying handles, together with the alternately collapsible and rigidifiable casing, provides a relatively lightweight, compact and inexpensive immobilizer support.

The immobilizer support is inexpensively fabricated by heat sealing plastic top and bottom casing sheets together to form the casing. In addition, upper and lower stiffener sections of plastic are heat sealed to the bottom casing sheet to define pockets for the stiffener means, and handle sections for the carrying handles are similarly heat sealed to the upper and lower stiffener sections. The handle portions are specially reinforced so that the immobilizer support can even be inverted under special circumstances without failure of the handles.

The immobilizer support is a form of vacuum evacuable "mattress" which cradles and supports a patient in a way which eliminates pressure points and uniformly distributes his or her weight without padding in the traditional sense. The support also provides insulation against escape of patient body heat. It enables a patient to be handled and transported in a prone or seated position, as required, with absolute immobilization of joints.

The advantages attendant use of the present support have greatly expanded its use beyond emergency and paramedic applications. It effectively supports and immobilizes a patient having accident related injuries or having disease-caused infirmities like the severe connective tissue deterioration of Marfan syndrome. It is helpful for a patient plagued by almost any kind of affliction that requires immobilization, particularly when lifting or transporting the patient for treatment, diagnosis or for personal needs.

Other aspects and advantages of the present invention will become apparent from the following more detailed description taken in conjunction with the accompanying drawings.

BRIEF DESCRIPTION OF THE DRAWINGS

FIG. 10 is a view similar to FIG. 2, but illustrating a second embodiment of the invention;

FIG. 11 is a view similar to FIG. 10, but illustrating a third embodiment;

FIG. 12 is an enlarged view taken along the line 12—12 of FIG. 11;

FIG. 13 is a detail bottom plan view of one of the handles and the adjacent casing structure;

FIG. 14 is an enlarged view taken along the line 14—14 of FIG. 11; and

FIG. 15 is a view similar to FIG. 14, but illustrating the handles in the positions they would assume when the present support is carried in an inverted position.

DESCRIPTION OF THE PREFERRED EMBODIMENT

Figure 6:
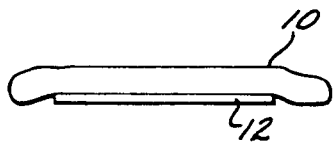
FIG. 6 is a prior art vacuum immobilizer support as it would appear when placed upon a standard backboard in the collapsed state of the support.
Figure 7:
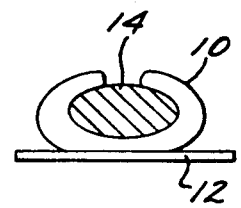
FIG. 7 is a view similar to FIG. 6, but illustrating the prior art support in its rigidified state partially overlying a patient.

Referring now to the drawings, and particularly to FIGS. 6 and 7, one prior art form of vacuum immobilizer support 10 is illustrated in position upon a standard or conventional spineboard or backboard 12 approximately 16 inches wide.

The support 10 is alternately collapsible and rigidifiable, being shown in its collapsed state in FIG. 6. It is approximately 30-34 inches wide, which makes it relatively heavy, bulky and therefore difficult to handle and store. It is made wide enough to substantially encircle the patient, as seen in FIG. 7. The resulting nearly cylindrical configuration of the rigidified support 10 provides structural resistance to bending when the support is lifted.

Figure 8:
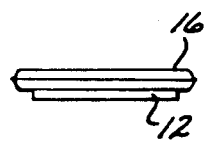
FIG. 8 is a view similar to FIG. 6, but illustrating the present vacuum immobilizer support as it would appear when placed upon a standard backboard in its collapsed state.
Figure 9:
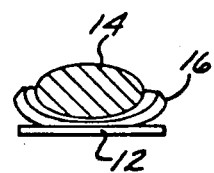
FIG. 9 is a view similar to FIG. 8, but illustrating the present support in its rigidified state partially extending up the sides of the patient.

The relative width of one form of support 16 according to the present invention is shown in FIGS. 8 and 9, the support 16 being shown in its collapsed and rigidified states, respectively. The support 16 is approximately 22 inches wide.

Referring now to FIGS. 1-5, the support 16 comprises, generally, an elongated airtight and flexible casing 18 upon which a patient can be placed. The casing includes neck and thoracic regions adapted to underlie the neck and thorax of the patient (not shown); evacuation valve means 20 enabling evacuation of air from the casing for developing a vacuum in the casing interior; stiffener means carried by the casing for preventing transverse bending of the casing in the neck and thoracic region and in the pelvic region and comprising an upper set of stiffeners, slats or battens 22 and a lower set of stiffeners, slats or battens 24. The casing further includes strap means in the form of a strap 26 for urging the sides of the casing against the patient's body 14. Located within the casing interior are a plurality of discrete elements or beads 28.

The casing 18 is formed of complemental top and bottom casing sheets 30 and 32 made of flexible, air impermeable synthetic plastic material sealed together at their edge margins by heat sealing or the like to define an airtight interior. A reinforcing strip 34 made of the same material as the sheets 30 and 32 is disposed about the edge margins of the sheets 30 and 32 and is stitched in place to strengthen the joint.

The sheets 30 and 32 are generally elongated and rectangular, although the end portions of the sheets can be made wider if desired to provide a generally hourglass shape. The wider end portions can then be used to store more beads 28, and are then wide enough to almost completely encircle the head and legs to better maintain them in position. However, the rectangular configuration illustrated is preferred for compact storage and ease of handling.

The sheets 30 and 32 can be made of any suitable material, fabric reinforced or otherwise, having adequate gas impermeability and wear characteristics. A woven nylon material with a protective coating such as urethane has been found to be satisfactory. This material provides a smooth surface for easy cleaning, and it is resistant to attack by chemical mixtures such as the oil, grease and gasoline often present at an accident site.

Upper and lower stiffener sections 36 and 38 of similar sheet plastic material are heat sealed at their edge margins to the bottom casing sheet 32 and define, respectively, a thoracic region and a pelvic region adapted to underlie the thorax and pelvis of the body 14.

The upper stiffener section also includes longitudinal heat seals defining a first plurality of transversely spaced pockets extending longitudinally through both the neck and thoracic regions of the casing. A plurality of the upper battens 22 are disposed in these pockets. In similar fashion the lower stiffener section is heat sealed to the bottom casing sheet 32 to define a second plurality of transversely spaced pockets extending longitudinally through the pelvic region of the casing. These pockets accept the lower battens 24.

Figures 1, 2:
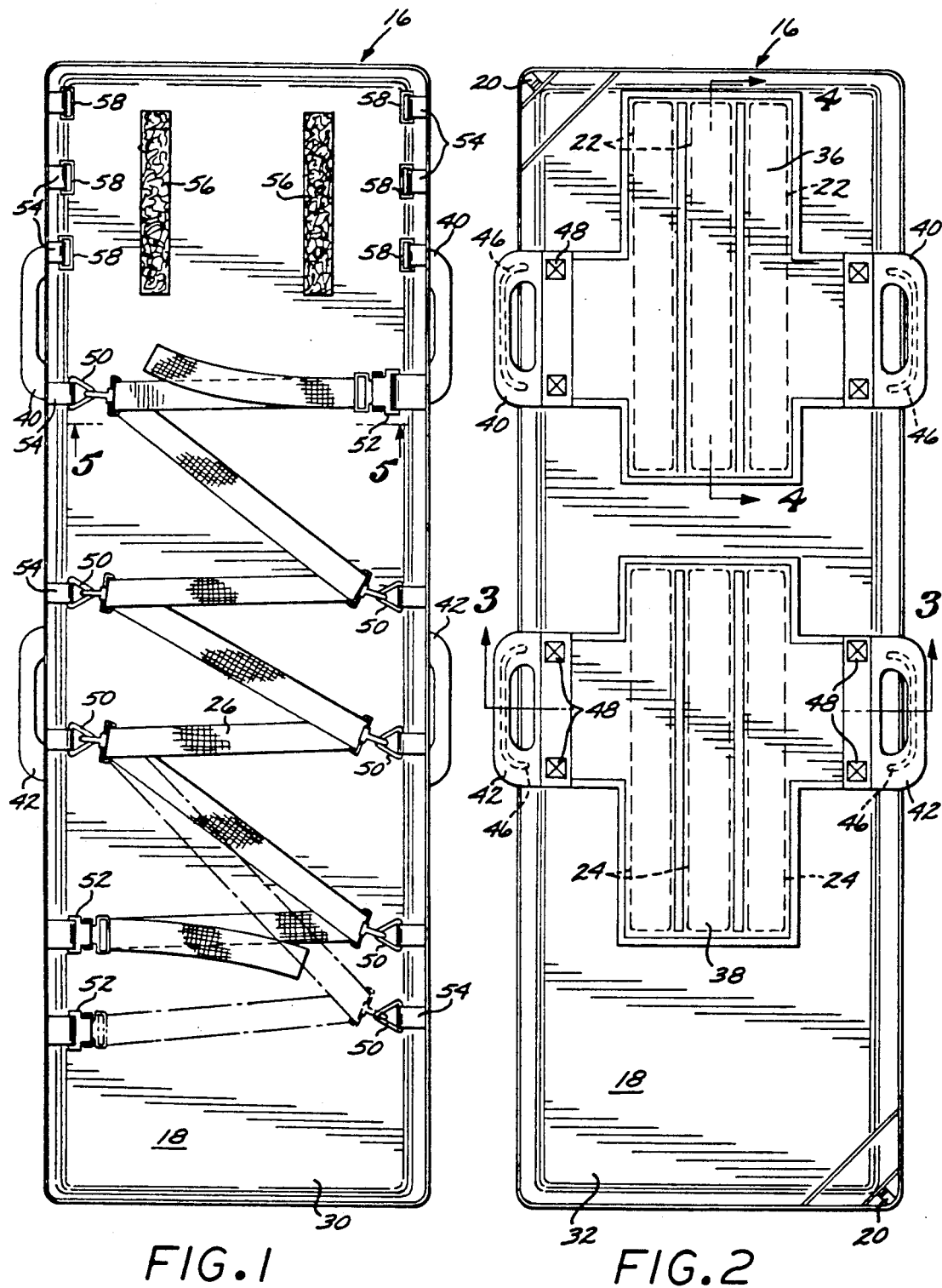
FIG. 1 is a top plan view of a vacuum immobilizer support according to the present invention.
FIG. 2 is a bottom plan view of the vacuum immobilizer support of FIG. 1.
Figure 3:
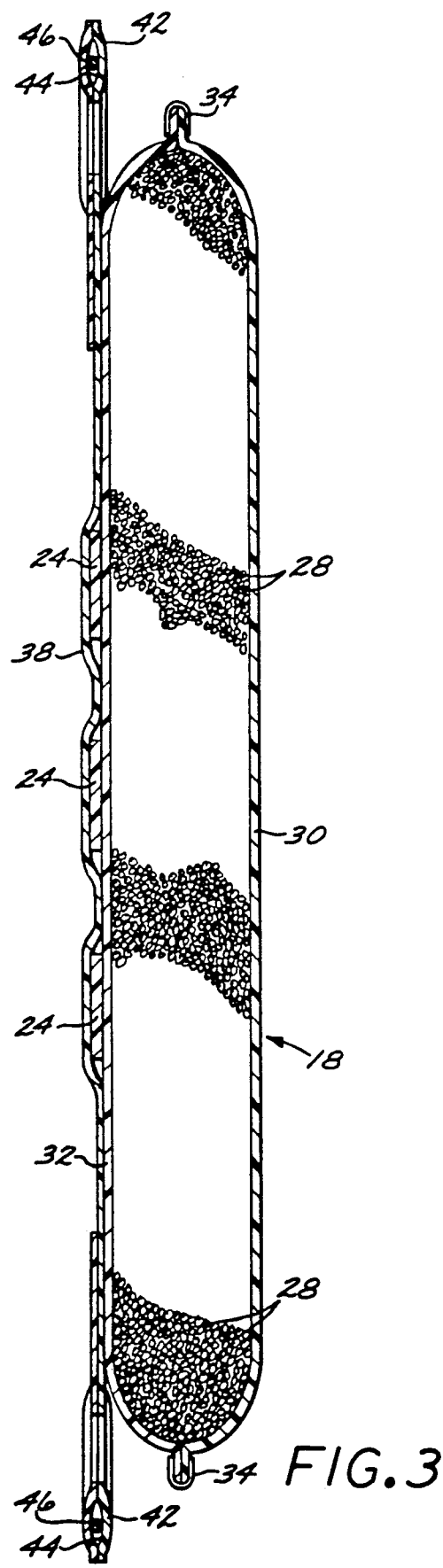
FIG. 3 is a view taken along the line 3—3 of FIG. 2.
Figure 4:
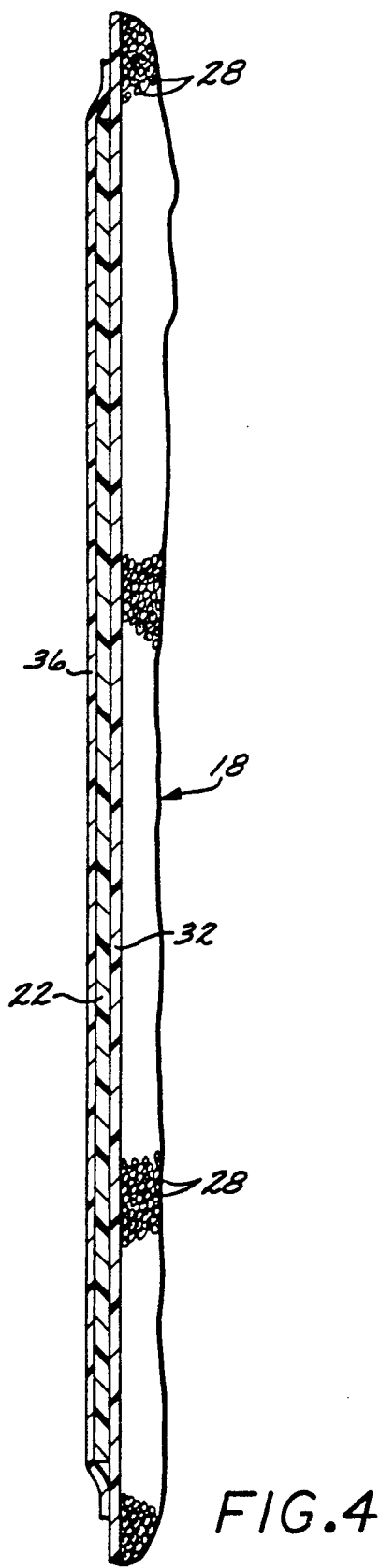
FIG. 4 is an enlarged view taken along the line 4—4 of FIG. 2.

As best seen in FIGS. 2 and 3, a first pair of handle sheet sections of sheet plastic material like that of the casing sheets are provided with hand openings. They are heat sealed together adjacent the hand openings and also to the side edge positions of the upper stiffener section 36 to define a pair of carrying handles 40 located in confronting relation on opposite sides of the thoracic region of the casing. Similar handle sheet sections are heat sealed to the side edge portions of the lower stiffener section 38 to define a pair of confronting handles 42 located on opposite sides of the pelvic region of the casing.

The heat sealing of the margins of the handle sheet sections leaves internal passages 44 adapted to receive U-shape reinforcing wires or rods 46, as seen in FIGS. 2 and 3, to better distribute lifting loads. The handle sections are also attached by suitable stitching, as seen at 48 in FIG. 2.

The other pair of handles 42 are located on opposite sides of the pelvic region. With this arrangement of handles 40 and 42 the weight of the patient is passed to the upper battens 22 located in the neck and thoracic regions, and to the lower battens 24 located in the pelvic region. The stiffeners prevent any transverse bending in these regions, provide support for the spine or lumbar vertebrae in the thoracic region, and provide support in the pelvic region from the coccyx downwardly to keep the patient's legs from rolling or flexing.

The casing interior is partially filled with a plurality of any suitable discrete elements or beads operative upon evacuation of the casing to rigidify the casing, as will be apparent to those skilled in the art. These beads can be made of expanded or solid plastic material, such as polystyrene or polyvinyl chloride. The loose beads and flexible casing permit the casing sides to be moved up against the sides of the patient to cradle and support the patient in position. The beads are then movable to conform to the contours of the patient's body, and also movable to regions where greater rigidity is required.

Figure 5:
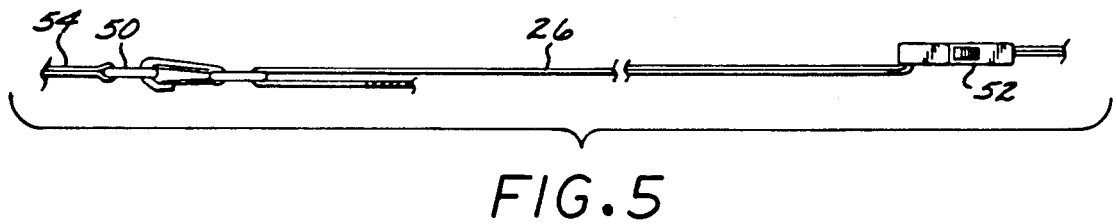
FIG. 5 is an enlarged view taken along the line 5—5 of FIG. 1.

A strap 26 is provided which is operative in conjunction with a plurality of strap fittings 50 and 52 to facilitate conforming the casing sides to the patient's body. As best seen in FIGS. 1 and 5, each strap fitting 50 is centrally apertured and generally triangular in configuration. It is conveniently supported by a fabric section 54 which extends through the aperture in the fitting and then around the edges of the casing sheets, where it is heat sealed or stitched in position.

A pair of the strap fittings 50 and 52 are located on opposite sides of the upper or head end of the casing. The fitting 52 of this pair is preferably located so that it aligns with the armpit of a patient properly oriented on the casing, and it is distinctively colored for this purpose. Emergency attendants can then quickly locate the patient so that the neck, thoracic and pelvic regions of the patient properly overlie corresponding regions of the casing.

The fitting 52 includes an apertured receptacle portion of generally rectangular configuration which, like the fitting 50, is mounted to the casing edge margins by a fabric section 54. The fitting 52 also includes an apertured insert portion carried by the upper end of the strap 26. The insert and receptacle portions of the fitting 52 are adapted to snap together and lock, but they are separable or releasable by applying pressure to the sides of the insert portion.

The upper end of the strap 26 is reversely formed and trained through the aperture in the insert portion of the upper fitting 52 in such a way that slack in the strap can be taken up by pulling on the end of the strap. However, the strap is constrained against movement in the opposite direction because of its reversed conformation in the insert portion of the fitting. Fittings of this type are well known in the prior art and will not therefore be described in further detail.

The receptacle portions of two other fittings 52 are attached by fabric sections 54 to the left side of the lower or foot end of the casing in longitudinally spaced apart relation. A pair of fittings 50 are similarly attached to the casing oppositely of these receptacle portions. The upper set of these fittings 50 and 52 is used for shorter patients, while the other set is used for taller patients, as indicated by the dotted line position of the strap 26.

The insert portion of the particular foot end fitting 52 used is attached to the lower extremity of the strap 26 in the same way as the insert portion of the upper fitting 52 is attached to the opposite extremity of the strap.

Pairs of oppositely located fittings 50 are longitudinally spaced along the edges of the casing 26 between the upper and lower complemental fittings 50 and 52. Each of the fittings 50 is attached to the casing by a fabric section 54, and is adapted to accept the hook of one of a plurality of slotted clips 60 which are slidably carried by the strap 26.

Each clip 60 is releasably snapped in place on its fitting 50 by a spring biased closure located adjacent the strap receiving slot of the clip. The clips 60 are carried on the strap 26 between the insert portions of the fittings 52 at the extremities of the strap. They correspond in number to the number of fittings 50. They are alternately oppositely oriented so that the openings to the clips are alternately oriented first one way and then oppositely. Preferably these are color coded, being alternately black and white, for example. As will be seen, this facilitates their proper placement.

In use, the insert portion of the fitting 52 on the upper extremity of the strap is snapped into the receptacle portion of the fitting 52 which is located at the upper right side of the casing. The attendant then reaches down the strap for one of the clips 60, sliding it up the strap and snapping it onto the upper fitting 50 opposite the upper fitting 52. Preferably this clip 60 is color coded white.

The attendant then grasps the next clip 60, which is preferably color coded black to indicate that it is oriented oppositely of the first clip 60. This opposite orientation is necessary for it to clip onto the next lower fitting 50 on the right of the casing. The strap 26 is diagonally oriented to reach this fitting 50, which is advantageous because the strap then provides support for areas of the patient that are located between the pairs of oppositely located fittings.

The next clip selected should be white, then clipped in place, and so on, until the straps extend across the patient's body transversely, then diagonally, etc., until the insert portion of the fitting lower extremity of the strap can be inserted into the receptacle portion of the lower fitting 52.

If the attendant selects a clip that is out of order and therefore not properly oriented for the fitting with which it is to be attached, this will become evident by the color coding, i.e. the white and black clips must alternate. This color scheme is particularly helpful in an emergency to save time in attaching the strap 26 in position.

One or both or both of the ends of the straps are next pulled to take the slack out of the strap. This brings the side edges of the casing into close conformity with the patient. The slack strap slides easily through the belt slots in the clips 60. This system eliminates the usual prior art plurality of transverse straps which have to be individually tightened.

Although the cradling and supporting action of the casing and beads is normally sufficient to immobilize the patient's head against movement, further support can be provided by employing a pair of plastic cushions or blocks (not shown) to serve as head immobilizers on opposite sides of the head. The undersides of such blocks typically include strips of "Velcro" material which are attachable to a pair of complemental Velcro strips 56 attached or adhered to the top casing sheet 30, as seen in FIG. 1. "Velcro" is a registered trademark for a patented product comprising a strip carrying plastic hooks removably attachable to a complemental strip of loop pile material.

Further head immobilization is provided by three head straps (not shown) extending across the patient's head and trained through apertures in suitable pairs of opposed strap fittings 58 attached to the heat sealed edges of the casing.

The valve means 20, as seen in FIG. 2, preferably comprises a pair of Schrader vehicle tire-type valves heat sealed in position upon the casing and opening into the interior of the casing. This type of valve is spring loaded and self closing. It can be connected either to a manual pump or a motor operated pump to evacuate air from the casing. The pump and valve can also be operated to admit air when the casing is to be collapsed.

FIGS. 10–15 illustrate two additional embodiments of the present vacuum immobilizer support. Each is characterized by additional stiffener means to provide greater support for the base of a patient's spine. Each is also characterized by improved handle structure adapted to support a patient in special situations where the patient and immobilizer support have to be inverted or turned over.

The embodiments of FIGS. 10 and 11 are substantially identical to that of FIG. 2. Accordingly, identical parts are assigned identical numerals, while parts which are not identical but which operate similarly are assigned the identical numerals with a subscript. The subscript "a" is used for the embodiment FIG. 10, and the subscript "b" is used for the embodiment of FIG. 11.

In FIG. 10 a transverse batten or stiffener 62 is shown disposed between the adjacent ends of the upper and lower battens 22 and 24. It is securely held in place by heat sealing a rectangular sheet of plastic material to the casing along a margin 64 to enclose the stiffener.

The stiffener 62 still allows the unevacuated casing 18 to be folded transversely, either just above or just below the stiffener, for the purposes described in connection with the embodiment of FIGS. 1 and 2, but it also serves the important functions of supporting the patient in the lower spinal region, and also preventing the longitudinal shortening of the casing which sometime occurs on evacuation. Such shortening is undesirable in that it compresses the spine.

In this regard, the upper and lower battens 22 and 24 serve a similar function in that they prevent the upper portion of the casing from pressing downwardly upon the patient's head, or upwardly upon the patients feet, respectively, when the casing is evacuated.

In the embodiment of FIG. 11 the stiffening arrangement to prevent longitudinal shortening of the casing comprises battens 22b and 24b. These are arranged in separate upper and lower sets which, as was true of the embodiment of FIG. 2, are longitudinally discontinuous. However, adjacent ends of the battens in each set are disposed within elongated batten sleeves 66. The sleeves 66 are longitudinally continuous from the upper extremity of the upper battens to the lower extremities of the lower battens and they are sufficiently longitudinally stiff or rigid that they prevent longitudinal shortening in the area between the upper and lower sets of battens. However, the batten sleeves 66 are transversely bendable in the area between the upper and lower sets of battens 22b and 24b.

Both the embodiments of FIGS. 10 and 11 are also characterized by differences in the handle structure, compared to the embodiment of FIG. 2. More particularly, as best seen in FIGS. 13–15, a web 68 of fabric is adhered to the underside of the inner extremity of each handle 42, is doubled back upon itself in stitched or adhering relation, and is then directed over the side of the casing 18 in non-adhering relation. The webs 68 extend and are stitched to the adjacent edges of the casing sheets 30 and 32, as seen in FIGS. 14 and 15.

The vacuum immobilizer support is normally carried so that the handles 42 are directed oppositely of the orientation illustrated in FIG. 14. However, if the patient and support need to be turned over or inverted, the webbings will then assume the loads, as seen in FIG. 15, and will prevent tearing or separation of the handles from the casing. If desired, the handles can be folded inwardly for storage, assuming the positions illustrated in FIG. 13.

In use, the relatively thin immobilizer support in its relaxed or collapsed state can easily be slipped beneath a patient or accident victim, with his or her armpit area positioned to lie adjacent the upper strap fitting 52.

Next, the insert portion of the upper fitting on the strap 26 is snapped into place and the clips 60 are successively snapped onto the fittings 50 in the proper order. The insert portion of the lower fitting on the strap is snapped into place and slack is taken up at one or both of the upper and lower fittings 52. This brings the sides of the casing upwardly and against the sides of the patient, as schematically indicated in FIG. 7. In its collapsed state the bag or casing can easily be formed to the contour of the patient's body, and the beads 26 shifted and packed into those areas where maximum support is needed. In this state it can also be bent transversely in the area between the battens 22 and 24 to accept a patient in a seated position so that when the casing is evacuated and thereby rigidified the patient can be extricated from or placed in a vehicle, lifted from or placed onto a wheelchair, or transported along a narrow flight of stairs.

The pump (not shown) is attached to one or both of the valves 60 and air is evacuated from the casing interior to rigidify the casing to maintain it in close conformity with the patient's body. In this rigid state the casing is incapable of transverse bending in the thoracic and pelvic regions because of the presence of the battens 22 and 24. Although in the unevacuated state of the casing it is bendable between the battens 22 and 24, this cannot occur in the evacuated state of the casing, not only because of its rigidity, but also because the weight of the patient is transferred from the carrying handles 40 and 42 to the battens 22 and 24.

In the embodiment of FIG. 10 the region adjacent the patient's spine is positively supported by the stiffener 62, and in both the embodiments of FIGS. 10 and 11 this region is also constrained against longitudinal shortening by the stiffener 62 and the batten sleeves 66, respectively.

When a patient is supported upon the rigidified support, it can be placed upon a standard backboard for transportation. At the hospital or other treatment facility the support can be lifted off the backboard and placed on a bed. Air can then be admitted to the casing interior through the valves 60. This allows the beads to move freely, collapsing the support so that it can be slipped out from beneath the patient.

If desired, the stiffener means can be made in the form of a single length of rigid material, such as a plywood panel, extending continuously from the neck region, through the thoracic region, and through the pelvic region. This would be less expensive than using a plurality of stiffeners, but such a structure would not be capable of transporting a patient in a seated state, nor would it allow the casing to bend along longitudinal axes and wrap over the sides of the patient.

From the foregoing it will be apparent that the present vacuum immobilizer support is uniquely adapted to cradle and support a patient in an immobilized state through evacuation of the bead filled casing interior. It has been found that the support uniquely prevents secondary trauma in the transportation of emergency or paramedic patients, in the transportation of patients in-hospital, and also in the support of wheelchair patients and those who are bedridden. The immobilizer support eliminates pressure points, and thermally insulates a patient who is then kept warm because of his or her own body heat. The firmness of support is easily varied by adjusting the degree of air evacuation from the casing.

If desired, the beads utilized can be made hollow and therefore compressible, which tends to prevent the formation of large wrinkles in the casing upon evacuation. Also, if desired, the lower set of battens could be divided into two groups of battens, one above and one below the knee area. This would enable bending of the unevacuated immobilizer support in the knee area.

Various other modifications and changes may be made with regard to the foregoing detailed description without departing from the spirit of the invention.

What is claimed is:

1. A vacuum immobilizer support comprising:
   an elongated, airtight and flexible casing upon which a patient can be placed, the casing having neck, thoracic and pelvic regions adapted to underlie the neck, thorax and pelvis of the patient;
   evacuation valve means enabling evacuation of air from the casing for developing a vacuum in the casing interior to convert the casing from a relatively flexible state to an evacuated state;
   stiffener means comprising an upper stiffener section in the neck and thoracic regions, a lower stiffener section longitudinally spaced from the upper stiffener section and located in the pelvic region whereby the casing is adapted to bend along a transverse axis located between the thoracic and pelvic regions in the relatively flexible state of the casing, and additional stiffener means located between the upper and lower stiffener sections and operative to prevent longitudinal shortening of the casing in the region between the upper and lower stiffener sections;
   strap means coupled to and adapted to extend across the casing for urging the sides of the casing against a patient on the casing to cradle and support the patient;
   a plurality of movable, discrete elements located within the casing interior and adapted in conjunction with the flexible casing in its relatively flexible state for movement into conformity with the contours of the patient, and further adapted to be rigidly fixed in position in an evacuated state of the casing for immobilizing the patient;
   a first pair of carrying handles located on opposite sides of the thoracic region; and
   a second pair of carrying handles located on opposite sides of the pelvic region.

2. A vacuum immobilizer support according to claim 1 wherein the additional stiffener means is a transversely oriented stiffener batten.

3. A vacuum immobilizer support according to claim 1 wherein the additional stiffener means comprises longitudinally continuous batten sleeves extending between the upper and lower extremities of the upper and lower stiffener sections respectively, and receiving the upper and lower stiffener sections.

4. A vacuum immobilizer support comprising:
an elongated, airtight and flexible casing upon which a patient can be placed, the casing having neck, thoracic and pelvic regions adapted to underlie the neck, thorax and pelvis of the patient;
evacuation valve means enabling evacuation of air from the casing for developing a vacuum in the casing interior to convert the casing from a relatively flexible state to an evacuated state;
stiffener means carried by the casing and preventing transverse bending of the casing in the neck, thorax and pelvic regions, the stiffener means including an upper stiffener section in the neck and thoracic regions, a lower stiffener section longitudinally spaced from the upper stiffener section and located in the pelvic region whereby the casing is adapted to bend along a transverse axis located between the thoracic and pelvic regions in the relatively flexible state of the casing, and a longitudinally incompressible intermediate stiffener section located between the upper and lower stiffener sections to prevent longitudinal shortening of the casing in the region between the upper and lower stiffener sections; and
a plurality of discrete elements located within the casing interior and adapted in conjunction with the flexible casing interior in its relatively flexible state for movement into conformity with the contours of the patient, and further adapted to be rigidly fixed in position in an evacuated state of the casing for immobilizing the patient.

5. A vacuum immobilizer support according to claim 4 wherein the intermediate stiffener section comprises a transversely oriented stiffener batten.

6. A vacuum immobilizer support according to claim 4 wherein the intermediate stiffener section comprises longitudinally continuous, longitudinal incompressible batten sleeves extending between and receiving the upper and lower extremities of the upper and lower stiffener sections.

7. A vacuum immobilizer support comprising:
an elongated, airtight and flexible casing upon which a patient can be placed, the casing having neck, thoracic and pelvic regions adapted to underlie the neck, thorax and pelvis of the patient;
evacuation valve means enabling evacuation of air from the casing for developing a vacuum in the casing interior to convert the casing from a relatively flexible state to an evacuated state;
stiffener means carried by the casing and preventing transverse bending of the casing in the neck, thorax and pelvic regions, the stiffener means including an upper stiffener section in the neck and thoracic regions, a lower stiffener section longitudinally spaced from the upper stiffener section and located in the pelvic region whereby the casing is adapted to bend along a transverse axis located between the thoracic and pelvic regions in the relatively flexible state of the casing, and a longitudinally incompressible intermediate stiffener section located between the upper and lower stiffener sections to prevent longitudinal shortening of the casing in the region between the upper and lower stiffener sections;
a plurality of discrete elements located within the casing interior and adapted in conjunction with the flexible casing interior in its relatively flexible state for movement into conformity with the contours of the patient, and further adapted to be rigidly fixed in position in an evacuated state of the casing for immobilizing the patient;
a first pair of carrying handles located on opposite sides of the thoracic region; and
a second pair of carrying handles located on opposite sides of the pelvic region, each of the first and second pair of handles being secured at its inner extremity to the underside of the casing for extension upwardly of the associated edge of the casing for grasping by a user to carry the support, and each of the handles including an elongated reinforcing strip attached at one extremity to the casing at the casing edge adjacent the handle, and attached at the other extremity to the handle and constraining the handle from separating from the casing when the support is carried in an inverted position.

* * * * *